Figure 1:
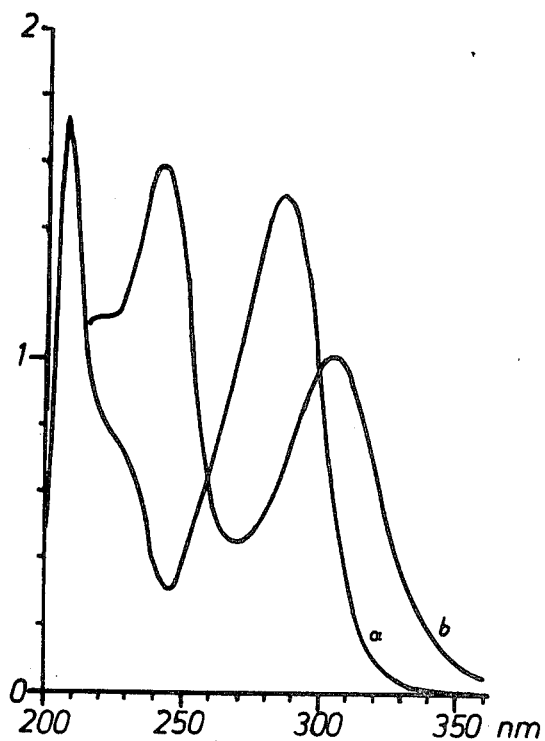

United States Patent [19]

Dähn et al.

[11] 4,158,608

[45] Jun. 19, 1979

[54] **FUNGICIDALLY ACTIVE ANTIBIOTIC FROM *STREPTOMYCES TENDAE* ETTLINGER**

[75] Inventors: Ursula Dähn, Filderstadt-Bernhausen; Hanspaul Hagenmaier, Tuebingen; Helmut Höhne, Bad Soden; Wilfried König, Pinneberg; Hans Scheinpflug, Leverkusen; Hans Zähner, Tuebingen, all of Fed. Rep. of Germany

[73] Assignee: Bayer Aktiengesellschaft, Leverkusen, Fed. Rep. of Germany

[21] Appl. No.: 785,729

[22] Filed: Apr. 7, 1977

Related U.S. Application Data

[62] Division of Ser. No. 669,780, Mar. 24, 1976, Pat. No. 4,046,881.

[30] Foreign Application Priority Data

Aug. 20, 1975 [DE] Fed. Rep. of Germany ....... 2537028

[51] Int. Cl.$^2$ .............................................. C12D 9/14
[52] U.S. Cl. ..................................... 195/80 R; 536/24
[58] Field of Search ..................................... 195/80 R

[56] References Cited

PUBLICATIONS

Chemical Abstracts, vol. 85, 18913q; 1976.
Chemical Abstracts, vol. 87, 20608d; 1977.
International Journal of Systematic Bacteriology; vol. 18, pp. 172-174; 1968.

*Primary Examiner*—Raymond N. Jones
*Assistant Examiner*—Robert J. Warden
*Attorney, Agent, or Firm*—Sprung, Felfe, Horn, Lynch & Kramer

[57] ABSTRACT

The new antibiotic Nikkomycin is produced by culturing the strain *Streptomyces tendae* Ettlinger et al Tü 901 in a nutrient medium at a pH of about 5.5 to 8 under aerobic conditions and isolation by cation exchange from the culture filtrate, followed by elution. The antibiotic is believed to have the structural formula

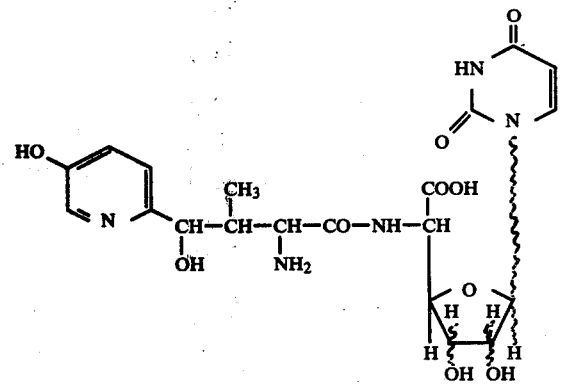

and is characterized by fungicidal activity.

2 Claims, 2 Drawing Figures

FUNGICIDALLY ACTIVE ANTIBIOTIC FROM STREPTOMYCES TENDAE ETTLINGER

This is a division of application Ser. No. 669,780, filed Mar. 24, 1976, now U.S. Pat. No. 4,046,881.

The present invention relates to a new antibiotic, a microbiological process for its preparation from strains of Streptomycetes and its use as a plant protection agent.

It has already been disclosed that polyoxines have found broad application as fungitoxic agents in plant protection. However, thier disadvantage is that they are labile to alkali and furthermore that they only occur as mixtures of varying composition and are therefore difficult to dose precisely, and to standardize.

It has now been found that the new antibiotic Nikkomycin can be obtained by aerobic culture of microorganisms of the order Actinomycetales, especially of the family of the Streptomycetaceae, and in particular of strains of the genus Streptomyces, in an aqueous nutrient medium, followed by isolation therefrom.

Further, it has been found that the new antibiotic Nikkomycin exhibits a powerful fungicidal action against phytopathogenic fungi.

Surprisingly, the antibiotic according to the invention has a substantially higher pH stability than the polyoxines known from the state of the art. Furthermore, it must be described as surprising that the new antibiotic Nikkomycin can be isolated as practically a single substance, because, in the light of the state of the art, it had to be expected that, similarly to the case of the polyoxines, a mixture of chemically similar substances would form during fermentation. Accordingly, the new antibiotic according to the invention represents an enrichment of the art.

The compound according to the invention is produced by submerged culture of suitable micro-organisms in suitable nutrient solutions under suitable physical conditions. It is isolated from the culture solution or, if appropriate, from the mycelium, by extraction, adsorption and precipitation, and is concentrated by further suitable methods.

The new strain *Streptomyces tendae* Ettlinger et al Tü 901 from the order of the Actinomycetales, family Streptomycetaceae, genus Streptomyces, can be employed for the process according to the invention. This strain has been isolated from a sample of soil from Nikko/Japan. It has been deposited under No. CBS 354.75 at the Centraalbureau voor Schimmelkultures, Baarn/Netherlands, under No. ATCC 31,160 at the American Type Culture Collection, Rockville, Md./USA and under No. FRI 3136 at the Fermentation Research Institute of Osaka/Japan. This strain belongs to the genus Streptomyces and is characterized by the following properties:

(a) The spores are ellipsoidal. They have a size of about $0.4$–$0.6 \times 1.2$–$1.4\mu$ and a smooth surface.

(b) The color of the aerial mycelium is initially chalk-white, and is ashen grey (cinereus) in the fully matured state. p1 (c) The spore chains are monopodially branched and arranged in loose spirals and loops.

(d) A black pigment was formed on peptone-iron agar at 27° C. The strain is chromogenic.

The summarized classification characteristics identify strain Tü 901 as belonging to the species *Streptomyces tendae* Ettlinger.

Nutrient media which contain the customary sources of carbon and sources of nitrogen and the requisite salts are used for the process according to the invention for the preparation of Nikkomycin. Sources of carbon which can be used are carbohydrates, especially polysaccharides, such as, for example, starch, disaccharides, such as, for example, maltose and sucrose, and monosaccharides, such as, for example, glucose and fructose. Furthermore it is possible to use sugar-alcohols, such as, for example, mannitol and glycerol, as well as naturally occurring mixtures, such as, for example, malt extract. Sources of nitrogen which can be used are the customary sources of nitrogen, such as, for example, proteins, protein hydrolyzates, amino acids, ammonium ions, nitrates, naturally occurring complex materials, such as peptones, casein hydrolyzates, corn steep liquor, soya flour, meat meal and meat extract, and suitable mixtures thereof.

Auxiliaries used in the nutrient medium are preferably the salts, for example phosphates, sulfates or chlorides, of magnesium, iron, zinc and manganese. The concentration of these compounds can vary within wide limits; in some cases, the requisite concentrations are contained as impurities in the abovementioned sources of carbon or sources of nitrogen or in the water used.

Furthermore it is possible to use, an auxiliaries, antifoaming agents of the most diverse kind, such as, for example, soya oil, polyols or silicones. To maintain a desired pH range, buffers are used, in the main inorganic phosphates and carbonates, but also organic buffers.

Water should be mentioned as the most important diluent for the nutrient media.

The process according to the invention is in general carried out under aerobic conditions; the culture can be carried out in accordance with customary methods, such as, for example, using shaken cultures or aerated fermenter cultures. The percentages of the nutrient solution constituents can vary within wide ranges; in general, the sources of carbon account for about 1 to 10%, preferably about 2 to 5% and the source of nitrogen account for about 0.1 to 4%, preferably about 0.5 to 2%; the salts are present in customary concentrations, preferably in the range of about 0.01 to 1% by weight. The anti-foaming agents are present in a concentration of 0 to about 1%. The temperatures used for the sterilization are about 100° to 140° C., preferably about 120° to 130° C.

The pH values of the growing cultures are about 5.5 to 8, preferably about 7 to 7.5. The culture temperature can be between about 18° and 37° C. and preferably about 27° to 30° C. It has been found that the amount of the antibiotic which accumulates in the culture broth in general reaches its maximum about 1 to 14 days, and preferably about 3 to 5 days, after the start of the culture. The end point of the incubation is determined by means of biological tests; in particular, the action against *Botrytis cinerea* (test method according to R. Hütter et al, Arch. Mikrobiol. 51, 1–8 [1965]) and *Mucor hiemalis* (test method according to the thesis by G. Kirst, Tübingen [1971], and also according to Kneifel et al, J. Antib. A 27, 20–27 [1974]) is determined.

In carrying out the process according to the invention, the culture solutions can be worked up by first carrying out the filtration, whereby the mycelium is separated off. The filtrate can be subjected to ion exchange chromatography on suitable exchangers. The chromatography can be carried out as column chromatography or preparative thin layer chromatography. As adsorbents it is possible to employ all customary (non-acidic) inorganic or organic adsorbents, such as, for example, aluminum oxide, silica gel, magnesium silicate, active charcoal, cellulose, cellulose derivatives, synthetic resins such as polyamides, derivatives of polyamides and the like, for example acetylated polyamide, or dextran gels. As migrating agents in preparative thin layer chromatography it is possible to use a great diversity of solvents or solvent mixtures in which the antibiotic according to the invention is soluble. Thereafter, gel chromatography, and isolation in the pure form on a further column, can be carried out, followed by freeze drying.

The antibiotic according to the invention, Nikkomycin, is new. It can be characterized by the following data:

(a) Solubility and properties: Nikkomycin is a colorless substance which is very readily soluble in water and pyridine and is insoluble in the other customary organic solvents. It gives a positive reaction with ninhydrin, sodium metaperiodate/benzidine and potassium permanganate. A yellow coloration is obtained with iron-(III) chloride.

Figure 2:
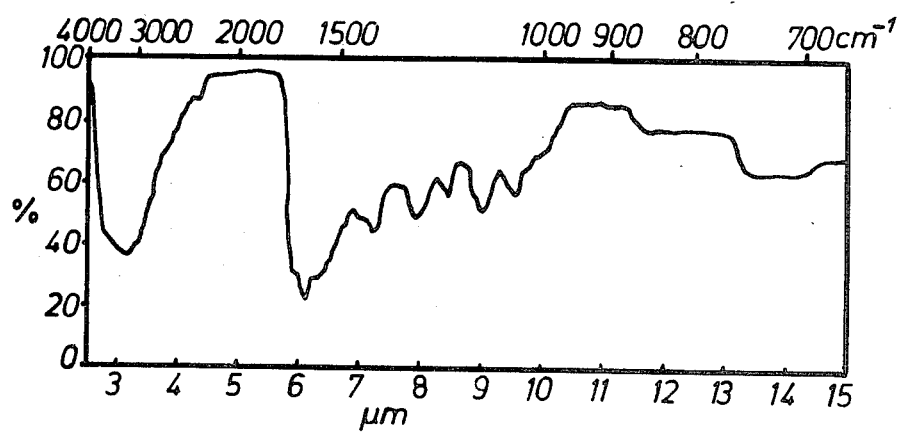

(b) The UV spectrum and the IR spectrum have been recorded (compare the corresponding representations in FIGS. 1 and 2). The UV spectrum of Nikkomycin, recorded in (a) 1 N hydrochloric acid and (b) in 0.1 N sodium hydroxide solution, is recorded in FIG. 1. The ordinate shows the extinction and the abscissa shows the wavelength (nm units). The IR spectrum of Nikkomycin, recorded in potassium bromide, is shown in FIG. 2. The ordinate shows the transmission in % and the abscissa shows the wave number (cm$^{-1}$) and wavelength ($\mu$m units).

(c) Uracil, an amino-hexuronic acid and a new amino acid containing a pyridine ring were detectable by means of mass spectrometry and of chemical degradation by acid hydrolysis.

(d) Paper electrophoresis: the antibiotic is amphoteric. Around a pH value of 6 the migration distance is small and accordingly this is probably the isoelectric point. The behavior of Nikkomycin on electrophoresis is shown in the Table which follows, in which the migration distances in paper electrophoresis are given as a function of the pH values of the buffer system.

| Buffer | pH | Time (minutes) | Migration distance (mm) |
|---|---|---|---|
| Pyridine/glacial acetic acid | 3.9 | 60 | −12 |
| Pyridine/glacial acetic acid | 6.1 | 60 | − 1 |
| 5,5-Diethyl-barbituric acid | 8.9 | 60 | +16 |

(e) Thin layer chromatography: here, three ninhydrin-positive spots are found in all the migration agents used, which contain acetic acid, and in each case only one spot corresponds with the substance which is active in the bioautogram. This fact was attributable to the labile nature of the antibiotic in acetic acid solution. In neutral migrating agents, only one ninhydrin-positive spot is found in each case.

(f) The following is proposed as the structural formula of Nikkomycin:

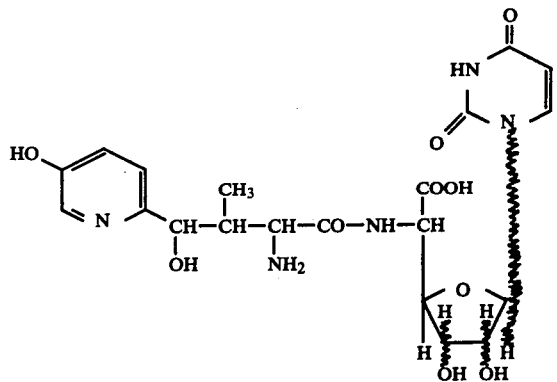

The elementary analysis of Nikkomycin gives the following values: C, 48.21; H, 5.08; N, 13.58; O, 31.58. From this, an elementary composition of $C_4H_5NO_2$ can be calculated. The molecular weight was found to be 404 by cryoscopic determination. However, the structure of Nikkomycin proposed above corresponds to a molecular weight of 495 and to the formula $C_{20}H_{25}N_5O_{10}=(C_4H_5NO_2)_5$. The elementary composition calculated therefrom gives: C 48.49%; H 5.09%; N 14.14%; O 32.29%.

(g) In contrast to the polyoxines known from the literature (compare J. Am. Chem. Soc. 91, 7490 [1961]), which are closest to Nikkomycin, the azacyclobutane radical is not present in Nikkomycin. The heterocyclic aminoacid is not present in any of the polyoxines described.

The active compound according to the invention exhibits a powerful fungitoxic action. It does not damage crop plants in the concentrations required for combating fungi and bacteria and has a low toxicity to warm-blooded animals. For these reasons, it can be used as a plant protection agent for combating fungi. Fungitoxic agents are employed in plant protection to combat Plasmodiophoromycetes, Chytridiomycetes, Zygomycetes, Ascomycetes, Basidiomycetes and Deuteromycetes.

The active compound according to the invention shows a particularly good action against rust diseases on various crop plants, such as species of Puccinia, species of Uromyces, *Phragmidium mucronatum*. Furthermore against species of Botyris, above all Botyris cinerea in vineyards, strawberry cultures and vegetable cultures, against species of Sclerotinia, against powdery mildew fungi, such as Erysiphe, and against species of Sphaerotheca. The active compound according to the invention can also be employed against species of Venturia, species of Alternaria, *Pellicularia sasakii, Pyricularia oryzae* and species of Cercospora. In addition to being used for the treatment of above-ground parts of plants, the active compound according to the invention can also be used to combat pathogens which attach the plants through the soil or are transferred with the seed.

The active material according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active material with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. Kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, or insecticides, acaricides, nematocides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.001–0.1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

In the treatment of seed, amounts of active compound of 0.1 to 10 g per kg of seed are generally employed, preferably 0.5 to 5 g. For the treatment of soil, amounts of active compound of 1–500 g per cubic meter of soil, preferably 10–200 g are employed.

Furthermore, the present invention contemplates methods of selectively killing, combating or controlling pests, e.g. fungi, which comprises applying to at least one of correspondingly (a) such fungi, and (b) the corresponding habitat thereof, i.e. the locus to be protected, e.g. to a growing crop, to an area where a crop is to be grown or to a domestic animal, a correspondingly combative or toxic amount, i.e. a fungicidally effective amount, of the particular active material of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active material utilized in admixture with the carrier vehicle will depend upon the intended application. Therefore, in special cases it is possible to go above or below the aforementioned concentration ranges.

The unexpected superiority and outstanding activity of the particular new material of the present invention are illustrated, without limitation, by the following examples:

EXAMPLE 1

Preparation of Nikkomycin

The nutrient solution in which the producer strain *Streptomyces tendae* Tü 901 is cultured is composed of 2% of soya flour and 2% of mannitol; the pH is adjusted to pH 7.5 before sterilizing. 10×500 ml Erlenmeyer flasks with 1 lateral intrusing, each containing 100 ml of nutrient solution, are inoculated with the producer strain and incubated for 48 hours at 27° C. on a rotary shaking machine at 120 revolutions/minute. A 10 l fermenter ("New Brunswick"), which contains 10 l of nutrient solution, is inoculated with this pre-culture and incubated at 220 revolutions/minute and 27° C., with an air supply of 4 l/minute, for 48 hours. A 100 l fermenter ("New Brunswick"), which contains 100 l of nutrient solution, is inoculated with this pre-fermenter and incubated at 150 revolutions/minute and 27° C., with an air supply of 450 l/minute, for 78 hours.

The culture, with the addition of 2% of a filter aid (Hyphlo Supercel ®, Johns Mansville), is pressed out by means of a filter press, first through a pre-clarifying filter (C 150, Schenk) and then through a post-clarifying filter (U 1,000, Schenk). The clear culture filtrate is acidified to pH 4.0 with acetic acid and charged onto a column (100×450 mm) filled with Dowex 50 W×4 ® cation exchange resin (50–100 mesh, Na+ form). The flow rate is 10 l/hour. The column is washed with deionized water until the liquid issuing from the column is completely colorless. The antibiotic is eluted with 30 l of 0.01 N ammonia and 30 l of 0.05 N ammonia. The biologically active eluate is freed from ammonia on a rotary evaporator, acidified to pH 4.0 with acetic acid and applied to a column (70×900 mm) filled with "Amberlite 252" ® cation exchange resin (Na+ form). The flow rate is 5 l/hour. The column is washed with deionized water until the liquid issuing from the column is completely colorless. The antibiotic is eluted with 15 l of 0.05 N ammonia. The biologically active eluate is freed from ammonia on a rotary evaporator, concentrated to a small volume (1 l), acidified to pH 4.0 with acetic acid and charged onto a column (25×850 mm) filled with SP-Sephadex C-25 dextran. The flow rate is 100 ml/hour. The column is washed with deionized water until an adsorption is no longer shown in the UV continuous flow detector at 280 nm (Uvicord II, LKB). Impurities are eluted with 0.01 M pyridine acetate buffer (pH 4.7) and the antibiotic is eluted with 0.02 M pyridine acetate buffer (pH 4.7). The biologically active fractions are combined, freed from the buffer on a rotary evaporator and concentrated to a very small volume. The concentrate (10 ml) is charged onto a column (25×1,500 mm) filled with Bio-Gel P 2 cellulose (200–400 mesh) and eluted with deionized water. The flow rate is 100 ml/hour. The purity is checked by detection at 280 nm using a UV continuous flow detector. The biologically active fractions are combined and lyophilized in a freeze-drying unit.

In the foregoing Example, the sources of the trade-marked auxiliaries and technical instruments were as follows:

(a) Fermenter from Messrs, New Brunswick Scientific Corporation Inc., New Brunswick, N.J./USA.
(b) Hyphlo Supercel ®, Messrs. Johns, Mansville, Cal., USA.
(c) Filter presses C 150 and U 1,000 from Messrs. Schenk, Filterbau (Filter Constructors), Schwäbisch-Gmünd, West Germany.
(d) Dowex ®, a trademark of Messrs. Dow Chemical Co., Midland, Mich./USA.
(e) Amberlite ®, a trademark of Messrs. Rohm and Haas Co., Philadelphia, Pa./USA.
(f) SP-Sephadex ®, a trademark of Messrs. Pharmacia Fine Chemicals, Upsala/Sweden.
(g) Unicord ® II, Messrs. LKB, Bromma, Sweden.

EXAMPLE 2

Shoot treatment test/cereal rust/protective (leaf-destructive mycosis)

To produce a suitable preparation of active compound, 975 parts by weight of water are taken and 25 parts by weight of dimethylformamide and 0.06 part by weight of emulsifier (alkylaryl polyglycol ether) are added. The active compound is diluted to the desired final concentration with this mixture containing water, dimethylformamide and emulsifier.

To test the protective activity, one-leaved young wheat plants of the Michigan Amber variety are inoculated with a uredospore suspension of Puccinia recondita in 0.1% strength aqueous agar. After the spore suspension has dried on, the wheat plants are sprayed with the preparation of active compound until dew-moist and are placed, for incubation, in a greenhouse for 24 hours at about 20° C. and 100% atmospheric humidity.

After 10 days' dwell time of the plants at a temperature of 20° C. and 80–90% atmospheric humidity, the occurrence of rust pustules on the plant is evaluated. The degree of infection is expressed as a percentage of the infection of the untreated control plants. 0% denotes no infection and 100% denotes the same degree of infection as in the case of the untreated control. The active compound is the more active, the lower is the degree of rust infection.

The active compounds, active compound concentrations in the spray liquor and degrees of infection can be seen from Table 1 which follows:

Table 1

Shoot treatment test/cereal rust/protective

| Active compound | Active compound concentration in the spray liquor in % by weight | Infection in % of the untreated control |
|---|---|---|
| untreated | | 100 |
| (structure shown) (known) | 0.0025 | 70 |
| Polyoxine | 0.001 | 0 |
| | 0.00025 | 20 |
| (known) | 0.0001 | 70 |
| Nikkomycin | 0.001 | 0 |
| | 0.00025 | 15 |
| | 0.0001 | 45 |

EXAMPLE 3

Botrytis test (beans)/protective

Solvent: — parts by weight
Dispersing agent: — parts by weight
Water: 100 parts by weight The amount of active compound required to give the desired concentration of active compound in the spray liquor is mixed with the stated amount of the solvent and the concentrate is diluted with the stated amount of water, which contains the stated additives.

Plants of Vicia faba having 2 to 4 pairs of leaves are sprayed with the spray liquor until dripping wet. After 24 hours, 2 pairs of leaves are taken off each plant and are in each case placed in a Petri dish lined with moist filterpaper. Filterpaper discs of 1 cm diameter are then dipped into an aqueous conidia suspension of *Botrytis cinerea* and laid on the leaves. The dishes are sealed. After an incubation time of 48 hours and an incubation temperature of 20° C., the necroses visible under the discs are rated according to frequency of occurrence. The ratings obtained are converted to percent infection. 0% means no infection and 100% means that the plants are totally infected.

The active compounds, active compound concentration and results can be seen from Table 2 which follows:

Table 2

| | Botrytis test (beans)/protective | |
|---|---|---|
| | Infection in % at an active compound concentration of | |
| Active compound | 0.0062% | 0.0031% |
| Polyoxine (known) | 31 | 80 |
| Nikkomycin | 12 | 16 |

EXAMPLE 4

Uromyces test (bean rust)/protective

Solvent: — parts by weight
Emulsifer: — parts by weight
Water: 100 parts by weight The amount of active compound required for the desired concentration of active compound in the spray liquor is mixed with the stated amount of the solvent and the concentrate is diluted with the stated amount of water which contains the stated additives.

The young bean plants, which are in the 2-leaf stage, are sprayed with the spray liquor until dripping wet. The plants remain in a greenhouse for 24 hours at 20°–22° C. and a relative atmospheric humidity of 70% in order to dry. They are then inoculated with an aqueous uredospore suspension of the causative organism of bean rust (*Uromyces phaseoli*) and incubated for 24 hours in a dark humidity chamber at 20°–22° C. and 100% relative atmospheric humidity.

The plants are then set up in a greenhouse under intensive illumination for 9 days at 20°–22° C. and a relative atmospheric humidity of 70–80%.

10 Days after the inoculation, the infection of the plants is determined in % of the untreated but also inoculated control plants.

0% denotes no infection and 100% denotes that the infection is just as high as in the case of the control plants.

The active compounds, active compound concentrations and results can be seen from Table 3 which follows:

Table 3

Uromyces test/protective

| Active compound | Infection in % of the infection of the untreated control at an active compound concentration (in %) of 0.0031% |
|---|---|
| (structure shown) (known) | 60 |
| Nikkomycin | 31 |

It will be appreciated that the instant specification and examples are set forth by way of illustration and not limitation, and that various modifications and changes may be made without departing from the spirit and scope of the present invention.

What we claim is:

1. A process for the preparation of the antibiotic Nikkomycin which comprises culturing the strain *Streptomyces tendae* Ettlinger et al Tü 901 in an aqueous nutrient medium containing a source of carbon, nitrogen, hydrogen and oxygen under aerobic conditions at about 18° to 37° C. and at a pH of about 5.5 to 8 and isolating Nikkomycin from the culture.

2. The process according to claim 1, wherein culturing is effected at a pH of about 7 to 7.5, and isolation is effected by filtering the culture, passing the filtrate through a cation exchange resin, eluting the column and collecting the eluate.

* * * * *